United States Patent [19]

Yu

[11] Patent Number: 5,818,902
[45] Date of Patent: Oct. 6, 1998

[54] INTENSITY MODULATED ARC THERAPY WITH DYNAMIC MULTI-LEAF COLLIMATION

[75] Inventor: Cedric X. Yu, Bloomfield Hills, Mich.

[73] Assignee: Elekta AB, Stockholm, Sweden

[21] Appl. No.: 609,457

[22] Filed: Mar. 1, 1996

[51] Int. Cl.[6] .................................................... A61N 5/10
[52] U.S. Cl. ............................................. 378/65; 378/151
[58] Field of Search .............................. 378/65, 147, 150,
378/151, 152; 250/492.3, 505.1

[56] References Cited

U.S. PATENT DOCUMENTS

| | | | |
|---|---|---|---|
| 5,160,847 | 11/1992 | Leavitt et al. | 378/65 X |
| 5,351,280 | 9/1994 | Swerdloff et al. | |
| 5,394,452 | 2/1995 | Swerdloff et al. | |
| 5,418,827 | 5/1995 | Deasy et al. | |
| 5,442,675 | 8/1995 | Swerdloff et al. | |
| 5,555,283 | 9/1996 | Shiu et al. | 378/65 X |
| 5,596,619 | 1/1997 | Carol | 378/65 |

OTHER PUBLICATIONS

McGraw–Hill Encyclopedia of Science & Technology, 6th Edition, vol. 13, pp. 110, 112, and 126–129 (1987).
McGraw–Hill Encyclopedia of Science & Technology, 6th Edition, vol. 15, pp. 154 and 155 (1987).
McGraw–Hill Encyclopedia of Science & Technology, 6th Edition, vol. 2, p. 506 (1987).
McGraw–Hill Encyclopedia of Science & Technology, 6th Edition, vol. 10, pp. 568–571 (1987).
McGraw–Hill Encyclopedia of Science & Technology, 6th Edition, vol. 13, pp. 413 and 414 (1987).
McGraw–Hill Encyclopedia of Science & Technology, 6th Edition, vol. 15, pp. 138 and 139 (1987).
McGraw–Hill Encyclopedia of Science & Technology, 6th Edition, vol. 4, pp. 292–293 (1987).
McGraw–Hill Encyclopedia of Science & Technology, 6th Edition, vol. 18, pp. 28 and 29 (1987).

Primary Examiner—David P. Porta
Attorney, Agent, or Firm—Jack D. Slobod; Dwight H. Renfrew

[57] ABSTRACT

A method and apparatus for delivering optimized treatment plans to deliver relatively high doses of ionizing radiation to target tissues while minimizing dose to the surrounding healthy tissues. The present invention utilizes continuous gantry motion in which field shape, which is conformed with a multi-leaf collimator, changes during gantry rotation. Using multiple superimposing arcs, arbitrary two-dimensional beam intensity distribution at different beam angles can be delivered, giving arbitrary dose distribution in the patient to maximize the therapeutic ratio.

25 Claims, 9 Drawing Sheets

Gantry at -135 degrees

```
0 0 0 0 0 0 0 0 0 0 0 0 0 0 0 0 0 0
0 0 0 0 0 0 0 0 0 0 0 0 0 0 0 0 0 0
0 0 0 2 3 0 0 0 0 3 5 2 5 4 5 0 0 0 0
0 0 0 4 1 0 0 0 0 4 5 4 5 3 5 0 0 0 0
0 0 0 3 2 0 0 0 0 4 5 3 4 2 4 0 0 0 0
0 0 0 0 2 0 0 0 0 5 5 1 5 5 4 0 0 0 0
0 0 0 4 4 0 0 0 0 1 2 3 5 4 3 2 0 0 0 0
0 0 0 1 1 0 0 0 0 3 3 5 5 5 4 0 0 0 0
0 0 0 0 0 0 0 0 0 0 0 0 0 0 0 0 0 0
0 0 0 0 0 0 0 0 0 0 0 0 0 0 0 0 0 0
```

Gantry at 0 degrees

```
0 0 0 0 0 0 0 0 0 0 0 0 0 0 0 0 0 0
0 0 0 0 0 0 0 0 0 0 0 0 0 0 0 0 0 0
0 0 0 0 2 4 5 3 2 5 1 0 0 0 0 0 0 0 0
0 0 0 2 3 5 5 4 3 1 0 0 0 0 0 0 0 0
0 0 0 1 2 5 5 3 1 1 0 0 0 0 0 0 0 0
0 0 0 2 2 5 5 5 1 0 0 0 0 0 0 0 0 0
0 0 0 0 4 5 4 4 2 2 0 0 0 0 0 0 0 0
0 0 0 1 3 5 4 2 4 1 0 0 0 0 0 0 0 0
0 0 0 0 0 0 0 0 0 0 0 0 0 0 0 0 0 0
0 0 0 0 0 0 0 0 0 0 0 0 0 0 0 0 0 0
```

00 Gantry at -90 degrees

```
0 0 0 0 0 0 0 0 0 0 0 0 0 0 0 0 0 0
0 0 0 0 0 0 0 0 0 0 0 0 0 0 0 0 0 0
0 0 1 4 5 5 0 0 0 0 0 0 1 1 0 0 0 0 0
0 0 3 2 4 5 0 0 0 0 0 5 3 4 2 0 0 0 0
0 0 4 5 5 5 0 0 0 0 0 0 3 2 5 1 0 0 0 0
0 0 2 5 3 3 0 0 0 0 0 0 3 4 2 0 0 0 0 0
0 0 3 4 3 4 0 0 0 0 0 0 2 5 3 1 0 0 0 0
0 0 0 5 4 5 0 0 0 0 0 0 3 1 4 3 0 0 0 0
0 0 0 0 0 0 0 0 0 0 0 0 0 0 0 0 0 0
0 0 0 0 0 0 0 0 0 0 0 0 0 0 0 0 0 0
```

Gantry at 45 degrees

```
0 0 0 0 0 0 0 0 0 0 0 0 0 0 0 0 0 0
0 0 0 0 0 0 0 0 0 0 0 0 0 0 0 0 0 0
0 0 0 0 0 5 5 4 4 5 0 0 0 0 0 0 0 0 0
0 0 0 0 0 5 4 3 5 3 4 0 0 0 0 0 0 0 0
0 0 0 0 4 3 2 5 1 4 0 0 0 0 0 0 0 0
0 0 0 1 5 5 5 2 5 0 0 0 0 0 0 0 0 0
0 0 0 0 4 4 5 5 2 5 0 0 0 0 0 0 0 0 0
0 0 0 0 5 5 5 3 2 2 0 0 0 0 0 0 0 0 0
0 0 0 0 0 0 0 0 0 0 0 0 0 0 0 0 0 0
0 0 0 0 0 0 0 0 0 0 0 0 0 0 0 0 0 0
```

Gantry at -45 degrees

```
0 0 0 0 0 0 0 0 0 0 0 0 0 0 0 0 0 0
0 0 0 0 0 0 0 0 0 0 0 0 0 0 0 0 0 0
0 0 0 5 5 5 4 5 0 0 0 0 0 0 1 1 0 0 0 0
0 0 0 4 5 5 5 2 3 0 0 0 0 0 5 0 0 0 0 0
0 0 0 3 4 5 4 1 1 0 0 0 0 0 2 0 0 0 0 0
0 0 0 5 5 5 5 2 0 0 0 0 0 0 3 0 0 0 0 0
0 0 4 4 5 5 4 5 1 0 0 0 0 0 0 1 0 0 0 0
0 0 0 3 5 5 5 4 4 0 0 0 0 0 0 1 0 0 0 0
0 0 0 0 0 0 0 0 0 0 0 0 0 0 0 0 0 0
0 0 0 0 0 0 0 0 0 0 0 0 0 0 0 0 0 0
```

Gantry at 90 degrees

INTENSITY MODULATED ARC THERAPY WITH DYNAMIC MULTI-LEAF COLLIMATION

BACKGROUND OF THE INVENTION

1. Technical Field

This invention relates to radiation therapy. Particularly, the present invention relates to a method and apparatus for delivering optimal radiation dose to cancer patients to improve the therapeutic ratio. The apparatus of the present invention relies upon a radiation generating device equipped with a rotatable gantry and a computer controlled multi-leaf collimator. The method of the present invention is referred to as intensity modulated arc therapy. It combines irradiation with gantry rotation and change of radiation field shapes. Each such rotation delivers a focused radiation dose to the tumor site. Arbitrary three-dimensional radiation dose distributions can be delivered with multiple superimposing arcs.

2. Discussion

Radiation therapy is intended to irradiate a tumor to high levels of radiation dose such that the growth of the tumor is halted and, preferably, all tumor cells are destroyed. Where it is not possible to destroy all cells of a tumor, radiation therapy is employed to reduce the size of the tumor so that it may be surgically removed. Radiation therapy also complements surgical removal of a tumor by irradiating microscopic extensions of the tumor.

In certain situations, chemotherapy is used instead of surgical removal with radiation therapy. This combination minimizes the toxicity on healthy cells normally effected by high doses of chemotherapy drugs administered alone.

The delivery of radiation in radiation therapy is a skilled art in that, in cancer therapy, the objective is to destroy a tumor without causing irreparable radiation damage in normal body tissue which is adjacent to the target tissue. This is generally made possible because of the nature of the cancer cells which distinguish themselves by being quickly replicating relative to normal cells. It is during the reproduction stage that cancer cells are sensitive to ionizing radiation. Accordingly, tumor cells are more readily destroyed by ionizing radiation than are normal cells because of this sensitivity.

It is the ionizing radiation which causes the ionization of the cell's chemical components. As photons or electrons enter body tissue, some of the energy disrupts cellular function. (Most energy is converted into heat which carries no damaging biological effect.) As ionizing radiation traverses the tissue, it contacts atoms, which causes them to become excited. This process results in the breaking of molecular bonds, followed by biological damage and cellular destruction.

While the cellular destruction caused by ionizing radiation produces desirable lethal effects on abnormal, quickly dividing cancer cells, this is not desirable for healthy cells. Indeed, the greatest limitation to the broad scale use of ionizing radiation in a therapy of various cancers relates to the fact that in most cases the radiation beam has to traverse healthy tissues in order to reach the tumor, causing damage to the healthy tissues. While an increased dose of radiation would be useful in curing the patient, the dose is limited by the negative effects of radiation on the adjacent, normal healthy tissue. Complicating radiation therapy are the two types of organs, serial and parallel. In the former, radiation tolerance is generally high, but the entire organ (such as viscera) must be preserved to maintain minimum function. In parallel organs (such as the liver or the lungs), while in the latter tolerance is normally low, a substantial portion of the organ may be destroyed and the organ still remains minimally operative. Accordingly, the goal of radiation therapy has been to maximally irradiate the tumor while keeping the dose to adjacent structures under their tolerance or preserve part of the healthy structure such that enough of the organ is maintained so as to guarantee a minimal functional reserve.

In keeping with the goal of administering maximum amounts of radiation to the target tissue while minimizing the delivery of radiation to healthy organs surrounding the tumor, various techniques and devices have been employed.

Two general approaches are taken today to delivering radiation therapy. One is to use multiple fields, and the other is to employ arc therapy.

In using multiple fields, each radiation beam incident is at a different orientation from the next. Since these radiation beams overlap at the tumor site, a higher dose can be given to the tumor than to the normal structures. To minimize the exposure of healthy structures around the tumor to radiation, masks of lead alloy are employed to shape each field as the two dimensional projection of the treatment target.

At least two problems are associated with radiation therapy through the use of multiple fields, both of which are related to the use of only a few fields of exposure. One problem is that the dose to the healthy surrounding structure (which is roughly the tumor dose divided by the number of fields) is still too high. The other problem is that the ability to shape the high dose volume is limited. (For example, if four or fewer fields are used [as is typical], the tumor high-dose area is substantially like a box.) Another problem associated with the use of multiple fields is the length of time it takes to produce the alloy blocks, which is usually a matter of hours or days. Storage of the bulky blocks is also a problem.

In arc therapy, irradiation is combined with the rotation of the gantry of the radiation producing apparatus. During gantry rotation, the radiation field is set to a fixed rectangular shape. While delivering radiation to the target tissue, the relatively large field delivers the same amount of radiation to surrounding healthy tissue. The apparatus leaves in its path a cylindrically-shaped swath as it completes its arc around the patient.

However, arc therapy shares the burden of dose to all structure surrounding the tumor and maximal overlap of beams from all orientations. Again, at least two problems result. First, there is no discrimination between structures. Arc therapy treats all structures around the target tissue the same way, but, as noted above, not all tissue has the same tolerance. Second, the cylindrical shape of the delivered high dose is not the typical shape of the tumor.

The above-noted problem related to the fabrication and use of blocks in multiple field therapy is generally solved with a device known as a multi-leaf collimator. This device consists of opposing arrays of radiation-impregnable, movable leaves or veins placed in front of the radiation beam. By driving each vein into different positions, virtually any desired field shape can be achieved in radiation therapy.

While directed to solving the time and labor expenses related to the use of blocks, the multi-leaf collimator does not solve the problems associated with conventional treatment techniques, as discussed in the preview section.

Thus, it would be desirable to provide a means for accurately shaping the high dose volume to conform to the actual three-dimensional shape of the tumor while keeping the dose to all surrounding structures under their tolerance or keeping the unaffected volume larger than the required functional reserve.

SUMMARY OF THE INVENTION

Pursuant to the present invention, there is provided a method and system for improving local tumor control and to provide an increased cure rate for cancer patients. The present invention is coupled with advances in computer technology and linear accelerator design. These features allow for the new method of delivering three-dimensional conformal radiotherapy provided for in the present invention.

The present invention delivers high doses of ionizing radiation to the target tissues while minimizing dose to the surrounding healthy tissues.

In general, the present invention relates to a method for delivering optimized treatment plans to improve the therapeutic ratio. The present invention utilizes continuous gantry motion as in known arc therapy. However, unlike known arc therapy, the field shape, which is conformed with the multi-leaf collimator, changes during gantry rotation. The three-dimensional shape of the resultant high dose volume, which can only be cylindrical with known arc therapy, can take more complex forms.

The apparatus and method for delivering radiation therapy according to the present invention takes consideration of the differences in tolerance levels among the various normal body organs surrounding the target area.

The present invention also compensates for differences in homogenous overlapping structures. For example, if in one direction there is an air space in the body, the path to the tumor is less than if that space was filled with tissue. The present invention compensates for such density differences.

In addition, by taking consideration of the differences in normal structure tolerances and by compensating for the differences in homogenous overlapping structures, angle preferences are created.

Furthermore, by again taking consideration of the differences in normal structure tolerances and by compensating for the differences in homogenous overlapping structures, intensity preference within a beam angle may be created.

The present invention also provides a system of delivering the intensity-modulated arc therapy of the present invention.

The intensity-modulated arc therapy of the present invention combines spatial and temporal intensity modulation with the movement of the gantry. It can be shown that the dose conformity is theoretically equivalent to that achievable with slice-based treatment techniques. The present invention also presents advantages over tomotherapy.

As with tomotherapy or other sliced delivery schemes, the intensity modulated arc therapy can deliver beams with both spatial and temporal intensity modulations. In comparison with the sliced delivery schemes, intensity modulated arc therapy has many advantages. It is implemented on existing linear accelerators equipped with a multi-leaf collimator. Therefore, it maintains the flexibility of a linear accelerator. Electron beam therapy and traditional treatment methods can coexist using the same device. Non-transaxial arc treatments can be achieved to a certain extent and partial arc rotations are easily achievable. Since a tomotherapy machine is a specialized device, the conventional treatment cannot be delivered.

With tomotherapy, a photon beam generated at the X-ray target is collimated into a slit, most of the photons generated in the target will be blocked, resulting in inefficient beam delivery and long delivery time. With intensity modulated arc therapy, most of the target will be in the beam during the delivery, maintaining a high efficiency in utilizing the photons generated in the X-ray target.

With tomotherapy, the patient is required to be moved in his length direction to cover the entire treatment area. This increases the cost and complexity of treatment. With intensity modulated arc therapy, no additional patient transport mechanisms are required to move the patient from slice to slice. Eliminating the slicing also eliminates the problem of beam abutment between slices, and the cold and hot spot associated with the abutments. Theoretically, such an abutment problem among slices will be much more severe if patient motion between treatment slices is considered.

Finally, since the intensity modulation in tomotherapy relies on a set of leaves to open or close the slit beam, the resolution of the beam intensities is the slit width by the leaf width. For practical design, such resolution is on the order of 1 cm by 1 cm. The smooth three-dimensional target shape has to approximated by a collection of 1 $cm^3$ cubes. Therefore, the dose conformity is limited. Such limitation is most severe for smaller targets, which are more suitable for conformal treatment. For intensity modulated arc therapy treatments, the leaf travel is continuous in the length direction of the leaves. The field aperture in the leaf width direction is collimated by the backup jaws and is, therefore, also continuous. Therefore, intensity modulated arc therapy can deliver higher dose conformity than tomotherapy.

The steps for employing the therapy of the present invention are as follows. First is the optimization of a treatment plan that uses a beam every 1–5 degrees around the patient. Second, besides the beam energy and prohibiting angles, describe the beams at all angles (i.e., having intensity distribution). (Appropriate methods and algorithms are made for these first two steps.) Third, translate two-dimensional intensity distributions at all beam angles into arcs (i.e., field shape sequences, number of beam monitor units per shape, et cet.). Fourth, write the field shape sequences, the number of monitor units per shape, et cet., in the format required by the multi-leaf collimator controller and transfer the information to the controller. Fifth, deliver the dosage.

One of the key steps involved in creating optimized dose distributions using the present invention is directed to a method to convert the intensity distributions at all beam angles required by the treatment plan into multiple arcs. Translation is affected by: (1) Determining the angle of multi-leaf collimator veins along which the radiation fields are conformed such that the field shape formed by the veins best coincides with the preferred field shape for all the various beam angles; (2) segmenting the two-dimensional beam intensity distributions of all beam angles into multiple, one-dimensional ones, each aligned with a pair of multi-leaf collimator veins; (3) determining the openings of each opposed pair of veins and the sequence of opening such that no large movement is required between two successive beam angles; (4) at every beam angle, constructing from the sets of vein openings a stack of field shapes; and (5) constructing arcs from the stacks of field shapes by picking one shape from each beam angle.

The present invention also provides the simultaneous synchronizing of radiation delivery, gantry rotation, and field shape alteration. This synchronizing is accomplished by slaving rotation and changes in field shape to delivered radiation monitor units so that the delivery is immune to machine dose rate fluctuations.

Since there is no need to move the patient during treatment and radiation is not interrupted between different beam angles, the treatment is also very time efficient using the present invention. Total treatment time including patient set-up and irradiation is comparable to or shorter than conventional treatments. Beam delivery time is proportional to the number of arcs required, which depends on the number of intensity levels and the complexity of the intensity distributions. The total beam time may be further reduced with modifications of the linear accelerators and with improved algorithms for converting the intensity distribution into the arc field sequences.

BRIEF DESCRIPTION OF THE DRAWINGS

The various advantages of the present invention will become apparent to one skilled in the art by reading the following specification and by reference to the following drawings, in which:

FIG. 6 represents samples of intensity distributions required by the inverse treatment planning to deliver the prescribed dose constraints;

FIG. 9b illustrates a cumulative dose volume histogram produced by the treatment plan application of FIG. 9a;

FIG. 10b illustrates a cumulative dose volume histogram produced by the treatment plan application of FIG. 10a.

DETAILED DESCRIPTION OF THE PREFERRED EMBODIMENTS

Known arc therapy techniques rely upon a rotating gantry that produces a fixed radiation field shape on the patient which creates a cylindrical high dose region. The intensity-modulated arc therapy of the present invention provides a method and an apparatus for delivering an optimized dose of radiation for radiation therapy to a patient by rotating the radiation beam in an orbit around the patient and changing the field shape during delivery of the therapeutic radiation. Not only can the target shape be highly complex, but the treatment may be optimized to assign higher weights to more favored beam angles and favored areas within a beam based upon both anatomical and biological constraints. Therefore, for the same tumor dose, patients are exposed to less radiation toxicity.

Figure 1:
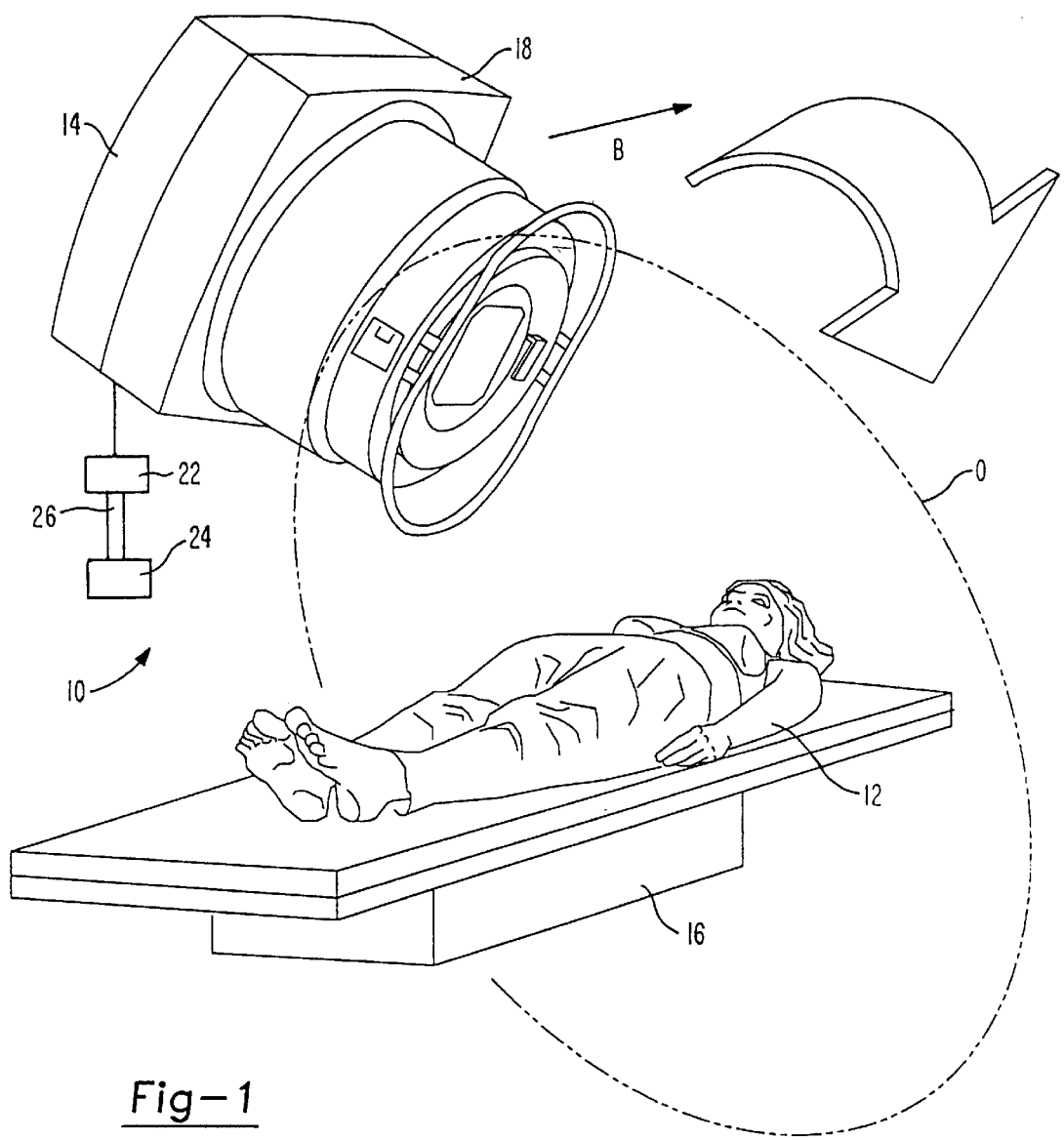
FIG. 1 is a perspective view illustrating a patient undergoing intensity-modulated arc therapy according to the present invention and further illustrating the general position of the apparatus for delivering the radiation and its general motions.

Referring to FIG. 1, an apparatus 10 used to provide intensity-modulated arc therapy to a patient 12 according to the present invention is shown. The apparatus 10 incudes a movable gantry 14 and a couch 16. The gantry 14 is mounted so as to allow revolution about the patient 12 as illustrated by the orbit "O" shown in broken lines. The gantry 14 is also movable along the long axis of the couch 16 as indicated by arrows "A" and "B".

Figure 1A:
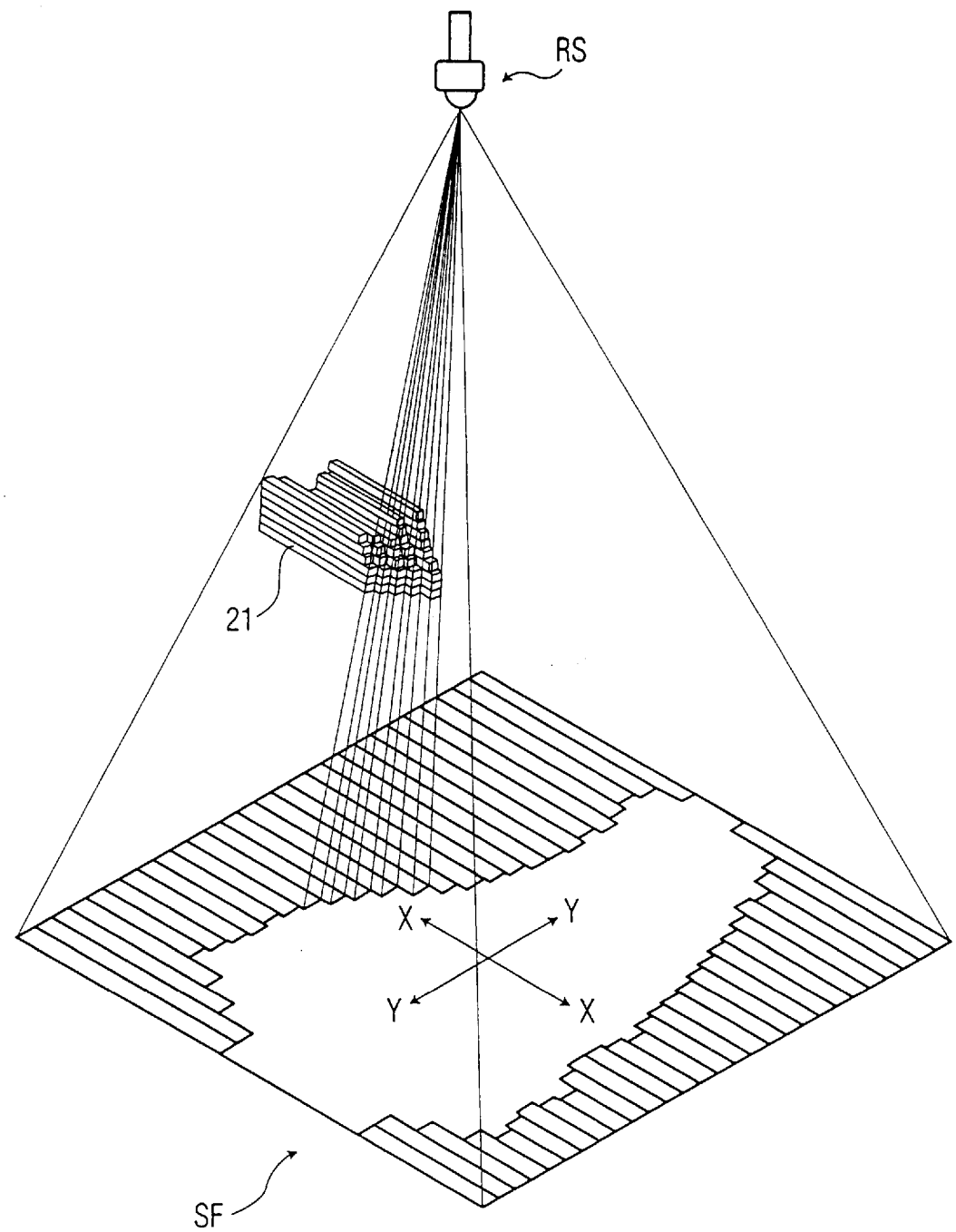
FIG. 1a is a diagrammatic perspective view illustrating a radiation field shaped by a multi-leaf collimator.

The gantry 14 is supported by a frame (not shown) that allows for both orbital and axial movement with respect to the couch 16. The gantry 14 itself comprises a radiation source 18 that includes a gas x-ray tube or a similar radiation source as is known to those skilled in the art. The gantry 14 further comprises a multi-leaf collimator 20 which consists of opposing arrays of narrow tungsten leaves or veins placed in front of a radiation beam. (These are illustrated in FIG. 1a.) The multi-leaf collimator 20 consists of several (preferably 40) pairs of opposing veins. By driving each vein into different positions, virtually any desired field shape can be achieved in radiation therapy.

FIG. 1a illustrates a diagrammatic perspective view illustrating a radiation field shaped by the multi-leaf collimator. A sample series of veins or leafs 21 are illustrated between a shaped field (shown for illustrative purposes and not intended to be limiting), generally illustrated as "SF", and a radiation source, generally illustrated as "RS". Each of the veins 21 of the multi-leaf collimator 20 is free to move along its length and projecting about 1 cm in width in the isocenter plane at about 100 cm from the source of radiation. Two pairs of back-up diaphragms (not shown) comprising solid tungsten jaws are provided complementary to the pairs of veins in the X and Y directions. The multi-leaf collimator 20 defines a maximum field size of about 40 cm×40 cm at the isocenter. A variety of geometric constraints affect collimation. These include permissible ranges of vein and diaphragm movements and minimum vein separation.

A video system and an image processor (not shown) are used to provide actual real time vein positions and dynamic vein motion capabilities. A multi-leaf controller 22 compares the actual vein positions with prescribed positions. A series of motors (not shown) operate to adjust the collimator 20 in response to the difference between these positions.

This prescription for each vein includes two positions: "start" and "stop". Only the "stop" position is compared with the actual vein position for static fields used for block replacement. In this event, the "start" position is set to "null". Also arbitrary is the number of monitor units to be delivered for a static field shape.

Between the multi-leaf collimation controller 22 and the linear accelerator 24 is provided a data link 26 which is included to accommodate dynamic vein motion. The multi-leaf collimation controller 22 converts the number of monitor units delivered by the linear accelerator 24 to a digital signal using an analog-to-digital connector (not shown).

The "start" position specifies the starting field shape and the "stop" position specifies the subsequent field shape. The "start" to "stop" prescription defines a "step" which has associated therewith a "dose-factor". The "dose-factor" represents the percentage of total monitor units that must be delivered within a particular "step". The sequences of subfields formed "steps" of one prescription. The controller 22 may also be used for spatial intensity modulation in a fixed field.

Fields and Subfields

As briefly noted, the intensity modulated arc therapy of the present invention is directed to the delivery of optimized dose distributions through the rotation of the radiation beam around the patient 12. The shape of the radiation field changes almost constantly during treatment.

According to the present invention, treatment is defined by several fixed fields at small angular intervals of rotation of the gantry 14. The two-dimensional intensity distribution generated at each beam angle by the inverse treatment planning techniques is regarded as a superimposition of multiple radiation fields of different sizes and shapes with each having a uniform intensity. Accordingly, a subfield for a given gantry angle is defined as being a uniform intensity beam which produces the two-dimensional intensity distribution at each beam angle, while an arc is defined as being a sequence of fields developed by taking one subfield from each beam angle with one arc delivering one level of intensity for all the beams at all the gantry angles. Several arcs are required to deliver the intensity distributions of multiple intensity levels.

Intensity Levels

A number of intensity levels required and the complexity of the intensity distributions dictates the number of superimposing arcs. Complexity is based upon the number of peaks and valleys or "island fields". Additional super imposing arcs may be required for complex intensity distributions. (A commercial treatment planning system, such as the "Peacock" system [Nomos Corporation], may be employed for establishing the treatment plan.)

The first requirement of a therapy of the present invention is to convert (or "decompose") the intensity distributions into multiple superimposing fields. Some methods of decomposition are known, but fail to satisfactory address the requirement of a smooth transition between two adjacent beam orientations within a field. The present invention overcomes these difficulties by providing an alternate approach to decomposing intensity distributions into multiple uniform subfields.

Two-Dimensional Intensity Distributions To One-Dimensional Intensity Profiles The initial step is to segment the two-dimensional intensity distributions at different gantry angles into multiple one-dimensional intensity profiles. Each of the one-dimensional profiles is aligned with a pair of opposing veins. There are a certain number of collimation angles along which the veins best conform the field shape for each subfield.

Collimator Angles

Different collimator angles may be required for subfields from different gantry angles and a variety of collimator angles may be used for different treatment plans. A common collimator angle avoids rotation of the collimator 20 during movement of the gantry 14.

Leaf Position

Figure 2A:
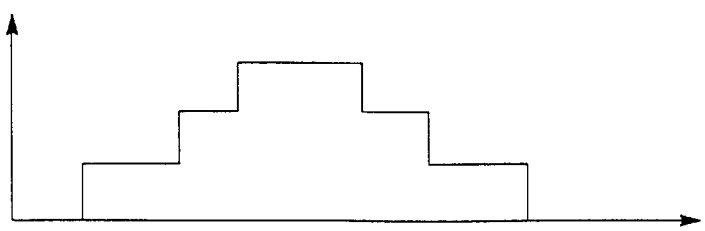
FIGS. 2a through 2d illustrate various ways to translate discreet beam intensity distributions into multiple unit-intensity fields with "intensity" being defined along the Y-axis and "position" being defined along the X-axis.
Figure 2B:
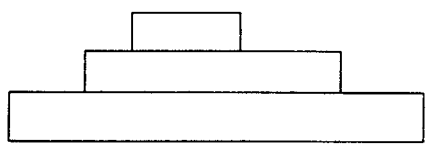
Figure 2C:
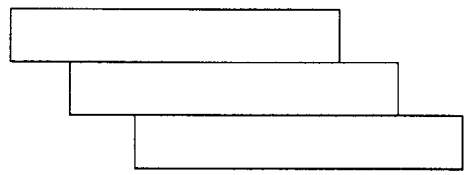
Figure 2D:
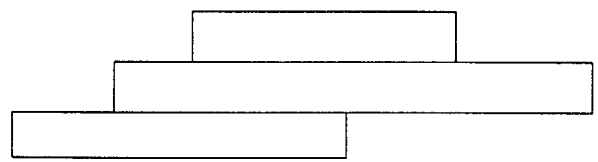

Each vein position for each vein pair in all of the subfields delivering a given beam intensity are then determined based on the one-dimensional intensity profile aligned with a given vein pair. FIGS. 2a–2d schematically illustrate an example of such translation at one gantry angle. More particularly, FIG. 2a schematically illustrates a simple, three level intensity distribution which may be delivered with those fields of different widths. Each field delivers a uniform intensity. The configurations of those fields may be of many patterns, and FIG. 2b illustrates the simplest of the choices which is derived by simply thresholding the input intensity distribution. The remaining FIGS. 2c and 2d show other possible subfield configurations.

Quantifying Decomposition Pattern For A Single Peak Intensity Profile

The arrangements of the series of subfields of FIGS. 2a–2d define "decomposition patterns". Such patterns determine (1) the vein positions of all subfields; and (2) the order of subfield delivery.

There are $(N!)^2$ decomposition patterns for an N-level intensity profile of only one peak. This is determined by reference to a one-dimensional intensity profile having intensity values which monotonically climb to a maximum level from both sides. When stratified into N discrete intensity levels such a "single-peak" intensity profile has N rising (left) and N declining (right) edges. Any pair of right- and left-hand edges defines a vein aperture for a subfield. A specific match of all the N right and the N left edges with a specific order of the N pairs of edges gives a decomposition pattern. The number of existent decomposition patterns depends on the number of different ways to pair the N left and the N right edges.

The number of existing ways to give one-to-one matches between N left and N right edges can be derived using proof by induction. More specifically, from the start the first left edge would have N choices to match a right edges. For each choice made by the first left edge, the second left edge would have (N−1) choices to pair to a right edge. Thus, for the first two left edges, there are N(N−1) different choices. For each of the N(N−1) choices made by the first two left edges, the third left edge would have (N−2) choices to pair to a right edge, and so on. Therefore, for the N-level single-peak profile, the number of ways that the N right edges pair with the N left edges is N(N−1) (N−2) . . . 1=N!. For each match of the N pairs of left and right edges, the pairs may be arranged in A=N! different orders.

Accordingly, and taking FIG. 2a as an example, there are 36 (derived from $(3!)^2=36$) possible different decomposition patterns. The computer algorithm used to generate the various decomposition patterns relies on the fact that each pair of left- and right-hand edges of an intensity profile determines a vein operation for a subfield. Each edge must be used once for efficient and complete decomposition. All of the $(N!)^2$ decomposition patterns may be generated by assigning indices to the edges of different intensity levels and by permitting the indices exhaustively.

The number of subfields for delivering a specific intensity profile is a function of the member of rising (left) or falling (right) edges in an intensity profile or on a number of intensity levels and the complexity of the intensity profile. Intensity profiles having only one peak have intensity levels with only one rising edge. For these profiles, the number of subfields needed is the same as the number of intensity levels. Intensity profiles having multiple peaks require more subfields.

The opposing edges of a pair of veins may need to be positioned as close to one another as possible for certain subfields when the closure of a vein pair is required and a passing therethrough of radiation is not desired. (Complete closure is not realistically possible due to the physical constraints of the curved form of the edge of the vein.) Because smooth beam delivery is important, the algorithm of the computer considers if the pair of veins that needs to be closed is at the edge of the field, and if this is found to be the case, back-up diaphragms (not shown) vertical to vein travel may be used to close the gap between the opposing veins. In the event that the pair of veins that needs to be closed is not at the edge of the subfield, any gap present between the opposing edges is divided into smaller gaps. The resulting smaller gaps are assigned to two subfields. Accordingly, the number of subfields at any given beam angle is dictated by the most complex one-dimensional intensity profile as defined by the two-dimensional intensity distribution.

Defining the Arc

The next step involved in the therapy of the present invention is formation of the particular arc. Arcs are formed by selecting one subfield from the stack of subfields at each beam angle in a top-down order. Because this step considers the number of subfields, it is noteworthy that the numbers of subfields at different gantry angles may also be different, thus the translation routine checks the location of the shortage of subfields. The possible shortage may be either at the beginning of the arc, at the end of the arc, or at the middle of the arc. If a shortage is at either the starting or the finishing end of an arc, the range of rotation of the gantry 14 for that arc will be accordingly adjusted so that it is shortened.

Conversely, if the shortage is in the middle of an arc, the translation routine checks how many neighboring beam angles have the same number of subfields. If this shortage of subfields lasts for more than a set range (for example, 25°), the arc is broken down into smaller ranges of rotation of the gantry 14. (If this step is not taken, an additional subfield will be created by dividing existing subfields into two or more pieces. This is why, as mentioned above, the number of arcs required is always determined by the most complicated beam intensities of all angles.)

Operational Efficiency and Decomposition Patterns

The method and apparatus of the present invention produce a large number of existent decomposition patterns which is necessary to make the described therapy feasible. It is also important that the veins not be required to travel very long distances by the subfields of adjacent beam angles. It is further important that overall beam time be reduced to a minimum. To achieve this end, high dose rate and high rotation speed of the gantry 14 may be used for arcs having similar field shapes.

While preferably a large number of existent decomposition patterns are produced by the described therapy, it is not necessary that each of the decomposition patterns be compared. In fact, the translation routine compares the decomposition patterns of a given beam angle to the finalized decomposition pattern of the previous beam angle, and once a decomposition pattern is found to register with that of the previous angle with spatial discrepancy less than a preset maximum, the translation routine accepts the pattern and proceeds to the next beam angle.

Leaf Movement

As noted above, smooth vein transition is important to effectiveness of the present therapy. To this end, the registration of the decomposition patterns of adjacent beam angles ensures smooth vein transition during rotation of the gantry 14. A substitute, less stringent registration is set if none of the decomposition patterns meets the registration criterion. The substitute registration results in longer vein travels between adjacent gantry angles, thus lowering the dose rate setting during beam delivery.

The sequences of vein positions for all of the arcs are written in the dynamic multi-leaf collimation prescription format as required by the collimation controller 22 once the decomposition patterns for all the beam angles are determined with consideration of all the physical constraints. In addition, a percentage of the total number of monitor units is also assigned to each subfield, and the entire multi-leaf collimation prescription is transferred to the multi-leaf collimation controller 22 through a network link (not shown).

In the event that the multi-leaf collimation controller 22 and the linear accelerator 24 are not integrated on one processing unit, the actions of both components must be synchronized properly for any dynamic treatments. The linear accelerator 24 is programmed to deliver conventional arc treatments and the multi-leaf collimation is programmed to step from one subfield to the next automatically to properly and effectively deliver arc treatments according to the present invention.

Both rotation of the gantry 14 and the vein stepping are slaved to the delivered monitor units. For smooth rotation of the gantry 14, the dose rate is preset to a constant based on the maximum vein transition between angles used in the intensity decomposition process. As the delivered monitor units increase, the gantry 14 is rotating continuously. Concurrently, the multi-leaf collimation is driving the veins from one subfield shape to the next. Because rotation of the gantry 14 and vein stepping are independently slaved to the different monitor units, gantry angle information is not needed by the multi-leaf collimation controller 22.

Leaf motion speed is proportional to the length of vein transition between the "start" and "stop" positions subject to the lower and higher limits. Because no precise speed control is applied to the veins, the shapes between two adjacent beam angles are not evenly interpolated. This is the case even though the shapes must be exactly the same as prescribed at each beam angle. Any resulting adverse effect from the uneven interpolation is reduced by either introducing precise speed control or by spacing the beams with smaller angular intervals.

Couch Angle

Figure 3:
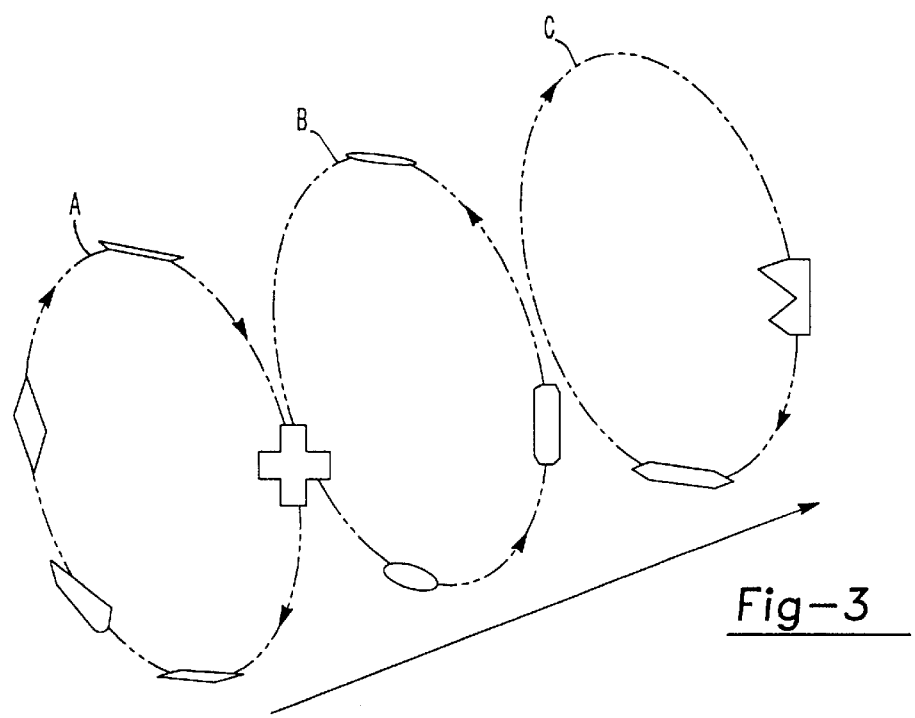
FIG. 3 is a diagrammatic view of some exemplary adjacent and coplanar gantry positions achieved according to the intensity-modulated arc therapy of the present invention.

Because there is no rotation of the couch 16 during rotation of the gantry 14, all the beams in the arcs are coplanar. This is illustrated in FIG. 3 which shows diagrammatically some exemplary adjacent and coplanar positions of the gantry 14 possible according to the present invention. Each of the coplanar arcs "A", "B", and "C" includes two or more exemplary field shapes. A couch and patient (not shown) would be axially positioned within the center of each arc.

A non-zero angle of the couch 16 would have to be selected if the treatment plan called for an arc treatment on a non-transaxial plan. The angle of the couch 16 in such a situation is limited by the clearance needed to avoid the collision between the collimator 20 of the gantry 14 and the patient 12. In any event, such a limitation does not appear to be a concern in that it is believed that non-transaxial plan treatments are unnecessary in intensity modulated arc therapy according to the present invention to deliver a specific dose distribution. (This is similar to the lack of necessity to angle the couch 16 when scanning a patient 12 with a CT unit.) However, it is possible that treatment along a non-transaxial plane may arise due to planning considerations other than dose distribution.

Controller Scheme

Figure 4:
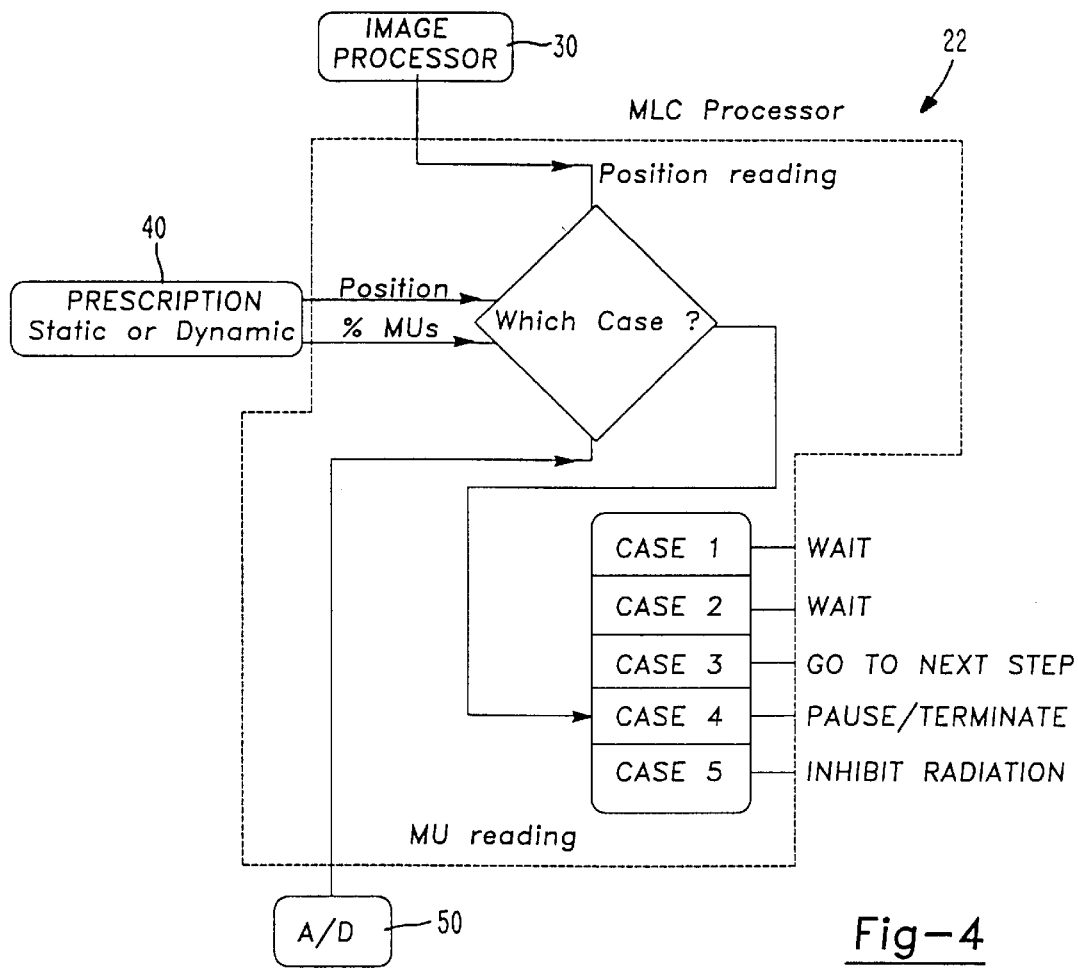
FIG. 4 is an illustration of the data processing and system control by the multi-leaf collimator controller during dynamic beam delivery.

FIG. 4 is a diagrammatic representation of the data processing and system control of the multi-leaf collimator 20 during dynamic beam delivery. Various inputs include the image processor 30, the prescription 40 (static or dynamic), and the analog/digital converter 50. At any instant, the multi-leaf collimation processor 22 compares the prescribed position and monitor units with the measured ones. Depending on the outcome of the comparison, the following actions are taken.

Case 1

If the delivered dose has not reached the desired level and the veins are not yet all in position, no action is taken.

Case 2

If the veins are all in position but the dose has not reached the desired level, again no action is taken.

Case 3

When all the veins are in position and the dose level is within tolerance of the desired value load the next step and move the veins to their new positions.

Case 4

If the dose level is reached but the veins have not been moved to their stop positions, the radiation is paused for a maximum of one second. This is done by turning the microwave power off through setting the pulse repetition frequency to zero which also halts movement of the gantry 14.

Two scenarios are possible at this point. If the veins reach position within this one second period, pulse repetition frequency and rotation of the gantry 14 are restored automatically. If the veins fail to reach position within the one second period, radiation will be terminated and must be restarted manually after the veins finally reach their positions. However, by presetting a dose rate that is low enough to accommodate the longest vein transition, this situation is generally avoided.

Case 5

In addition to the various scenarios of Case 4, radiation may be inhibited due to other interruptions. One such interruption may include a motion interrupt signal generated from the collision touch guard. Another may be an interruption by the user. In the event that the radiation is interrupted, the remaining steps and monitor units can be stored as new beams and subsequently restarted.

The present invention provides several advantages over known arc therapy techniques. For example, the above-described method and technique provides a simple immediate improvement over conventional arc therapy by using one intensity level and letting the field shape follow the beam's eye view of the planning target during rotation of the gantry 14. This provides high doses to target areas while minimizing doses to surrounding healthy tissues by excluding critical normal structures from the arc sequence.

Further, the present invention provides a quick and efficient way to deliver optimized treatment plans to improve the therapeutic ratio. As an additional advantage over the prior art, the complexity of the intensity modulated arc therapy according to the present invention is not significantly greater than existing arc therapy from the operator's point of view. Still further, since both spatial and temporal intensity modulation can be achieved, the dose conformity is significantly better than that with conventional treatments and potentially may also be better than that using multiple fixed fields with spatial intensity modulation.

The intensity modulated arc therapy of the present invention can deliver beams with both spatial and temporal intensity modulations similar to known sliced delivery schemes. In comparison with these schemes, intensity modulated arc therapy has many advantages. It is implemented on existing linear accelerators equipped with a multi-leaf collimation and thus maintains the flexibility of a linear accelerator 24. Non-transaxial arc treatments can be achieved to a certain extent and partial arc rotations are easily achievable. Since the technique of the present invention does not collimate the beam into a slit, most of the target will be in the beam during the delivery. This approach maintains a high efficiency in utilizing the photons generated in the X-ray target.

As a further advantage over sliced delivery schemes, no additional patient transport mechanisms are required to move the patient 12 from slice to slice. In addition, eliminating the slicing also eliminates the problem of beam abutment between slices and the cold and hot spots associated with the abutments. (Theoretically, such an abutment problem among slices will be much more severe if patient motion between treatment slices is considered.)

Finally, since the intensity modulation in tomotherapy relies on a set of veins to open or close the slit beam, the resolution of the beam intensities is the slit width by the vein width (commonly 1 cm×1 cm). For intensity modulated arc therapy treatments, the resolution is the width of the vein in the vein width direction and continuous in the length direction of the veins. The field aperture in the vein width direction is collimated by the back up jaws and is, therefore, continuous. If inverse treatment plans are optimized for intensity modulated arc therapy treatments, the beam intensities can be of higher resolution than that optimized for tomotherapy.

The invention will be better understood from a consideration of the following example.

EXAMPLE—PHASE 1

An intensity modulated arc therapy treatment was delivered using a phantom made of black plastic measuring 16 cm (W)×16 cm (L)×17.5 cm (H). The phantom consisted of an outer box and several plates contained within the box. The plates were all composed of an acrylic material and had radiation-sensitive films therebetween. The films were sandwiched between the plates in the plan of beam rotation. A C-shaped "target" which partially wrapped around a round "critical structure" was employed.

Figure 5:
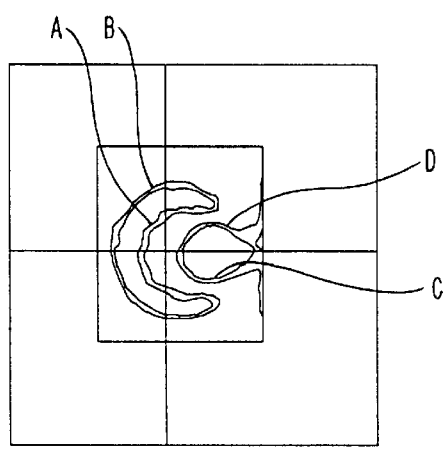
FIG. 5 is a treatment plan example used for the delivery of intensity-modulated arc therapy according to the present invention.

CT scans were first made for the phantom. The CT images were used by the above-described treatment planning system for inverse treatment planning. The treatment plan employed in the present Example is shown in FIG. 5. The treatment used 55 10 MV X-ray beams spread between −135° (225°) and 135° gantry angles at 5° intervals. The phantom was constructed according to the treatment plan.

As shown in FIG. 5, the isodose distribution normalized to the maximum dose resulting from the optimization is superimposed on one CT slice of the test phantom. The inner isodose contour on the C-shaped target, indicated as "A", is 90%, while the outer isodose contour on the target, indicated as "B", is 80%. The inner isodose contour on the circular critical structure, indicated as "C", is 10%, while the outer isodose contour on the structure, indicated as "D", is 20%.

The inverse treatment plan produced beam intensity distributions required to deliver the prescribed dose constraints to the C-shaped "target" for optimized treatment. A sample of the distributions generated are set forth in FIG. 6. Each of the density distributions was first decomposed into 13 subfields of unit intensity. The pixel size used was 1 cm×1 cm. Six pairs of multi-leaf collimation veins were used to deliver the 6 cm thick treatment volume. Optimization was made to minimize vein motion among adjacent fields at adjacent beam angles. The results were then written as 13 multi-leaf collimation field sequences representing 13 arcs in the format required by the multi-leaf collimation controller 22. The length of the arcs varied between 25 and 275 degrees of rotation of the gantry 14.

Dynamic multi-leaf collimation prescriptions were loaded in the same manner as for static treatments. The linear accelerator 24 was set as for conventional arc treatment. The gantry 14 was rotated at a constant speed and the collimation veins stepped through the prescribed field shapes once the radiation was started. All arcs were delivered with 0.1 MU/degree of rotation of the gantry 14 and a total of 250 MU were delivered with a beam time of approximately 4.5 minutes. Six MV X-rays were used for delivering the planned beam intensity distributions. (Although not undertaken in the present Example, by inputting the beam data of the linear accelerator 24 into the planning system, a quantitative comparison with the planned dose distribution may be made.)

Figure 7:
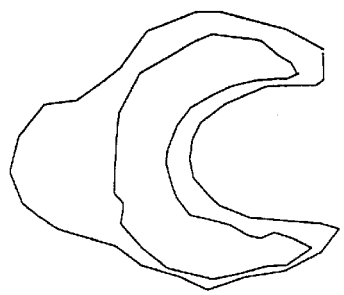
FIG. 7 is an image illustrating a delivered dose distribution pattern.

The resulting film images were scanned into a computer with the grey levels being converted to dose using a calibrated relationship. FIG. 7 shows the grey scale image of the resultant dose distribution. The light areas represent high-dose regions and the dark areas represent low-dose regions.

While results naturally vary, the intensity distributions demonstrated in the present Example are relatively complex having multiple intensity peaks and disjointed beam intensities. As may be understood, complex beam intensity distributions generally require more arcs to deliver.

EXAMPLE—PHASE 2

The number of intensity levels at each gantry angle has to be limited for the intensity modulated arc therapy of the present invention to be regarded as practical enough for general use. Both treatment time considerations and the lowest number of monitor units per degree of rotation of the gantry 14 allowed by the linear accelerator 24 dictate this requirement. Intensity levels can be limited by quantizing the required intensity distribution. Intensity levels can also be limited by setting distribution as a constraint during treatment plan optimization. Elimination of the quantization effects may occur when the number of intensity levels are set as one of the optimization constraints.

Figure 8A:
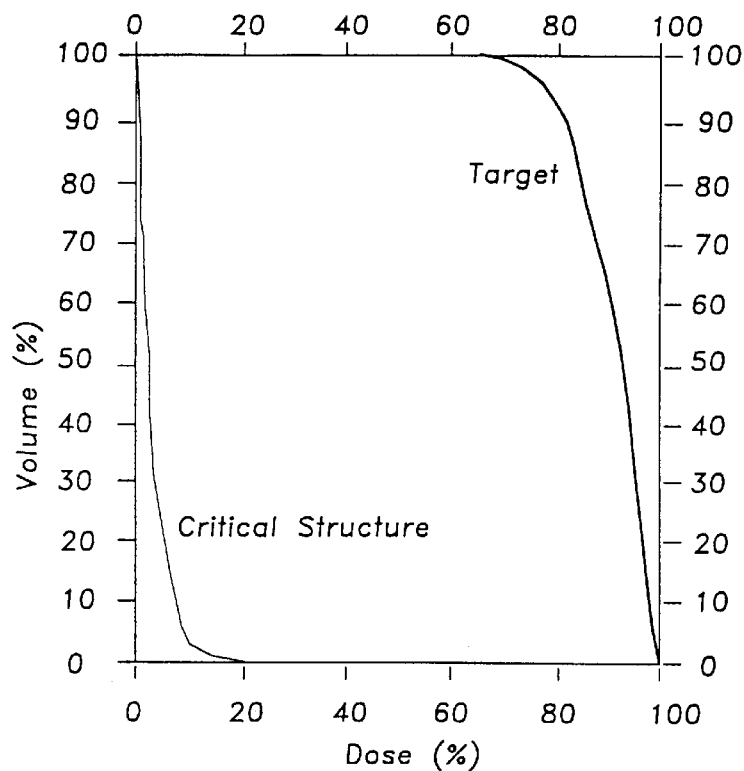
FIGS. 8a and 8b illustrate cumulative dose volume histograms calculated from the treatment plans.
Figure 8B:
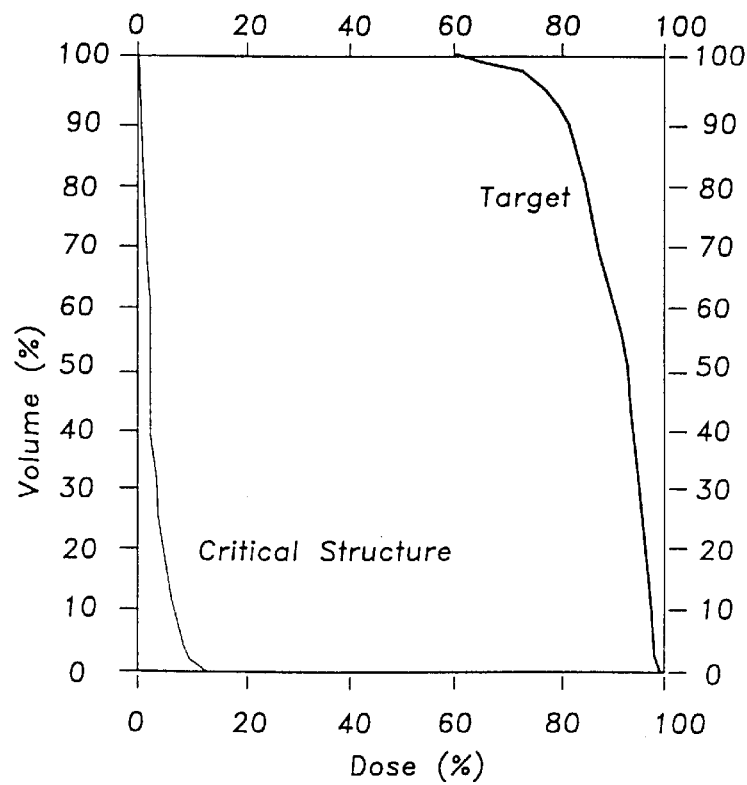

FIGS. 8a and 8b are calculated dose-volume histograms graphically illustrate the differences between beam intensities limited to five levels (FIG. 8a) and ten levels (FIG. 8b) for the test geometry of FIG. 5. The figures disclose slopes for both the C-shaped "target" and the circular "critical normal structure" of the intensity modulated arc therapy delivery Example set forth above. Volume-percent is set on the Y-axis and dose-percent is set on the X-axis. In both cases, the number of intensity levels is set as an optimization constraint in the treatment plan optimization using the NOMOS' PEACOCK treatment planning system discussed above.

Figure 9A:
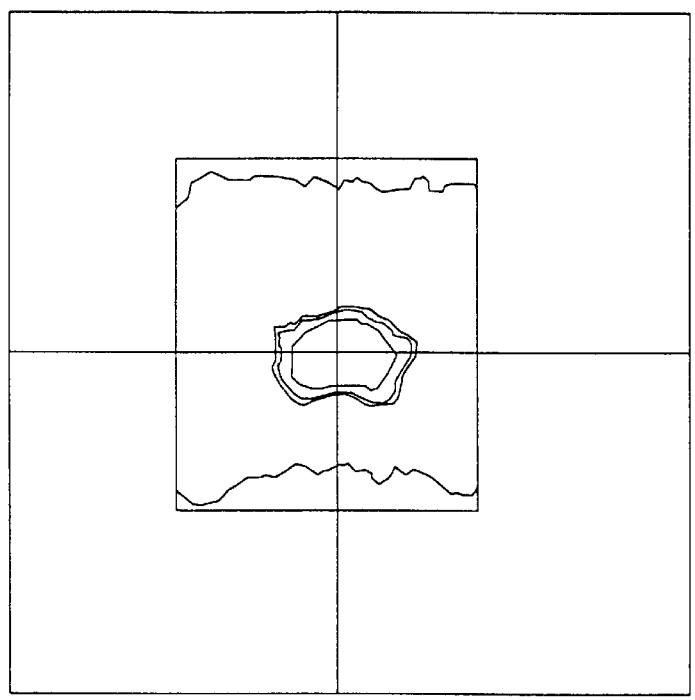
FIG. 9a illustrates a treatment plan application limited to five levels for a prostate treatment geometry.
Figure 9B:
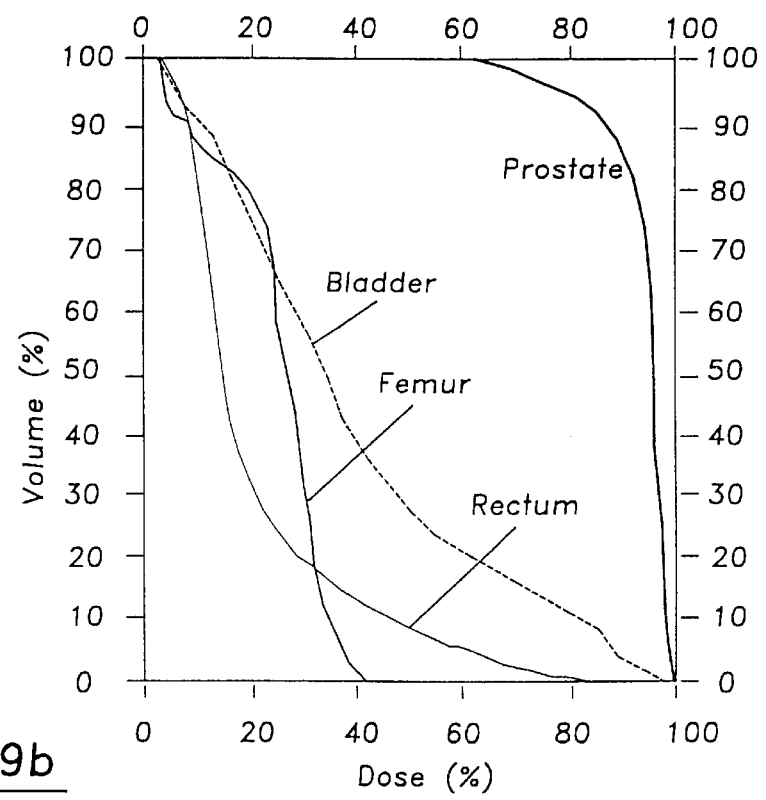

FIG. 9a is a view of prostate treatment geometry designed with the same phantom as the C-shaped "target" example set forth above in FIG. 5. The rectum, the bladder, and the femur are defined as critical structures. Beam intensity was limited to five levels. FIG. 9b is a dose-volume histogram for the prostate treatment geometry of FIG. 9a.

Figure 10A:
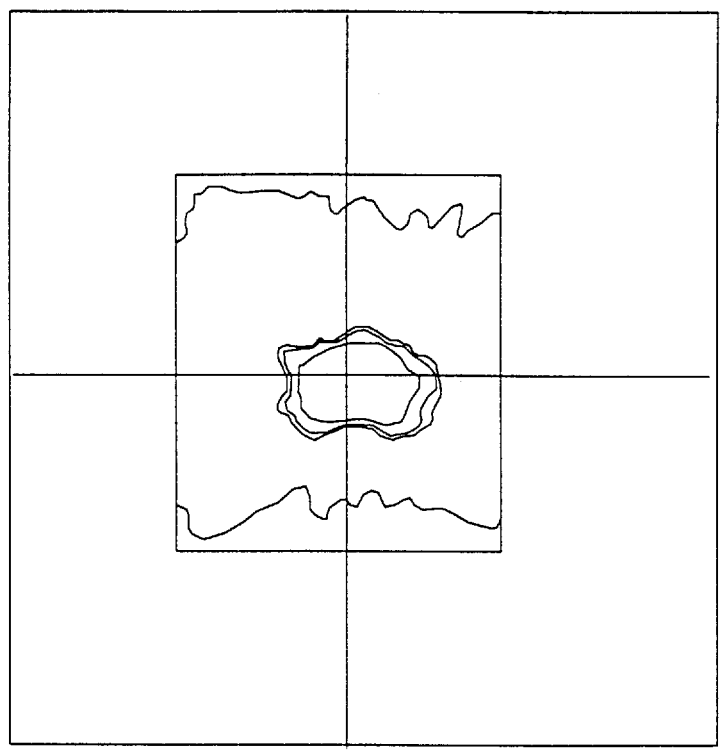
FIG. 10a illustrates a treatment plan application limited to ten levels for a prostate treatment geometry.
Figure 10B:
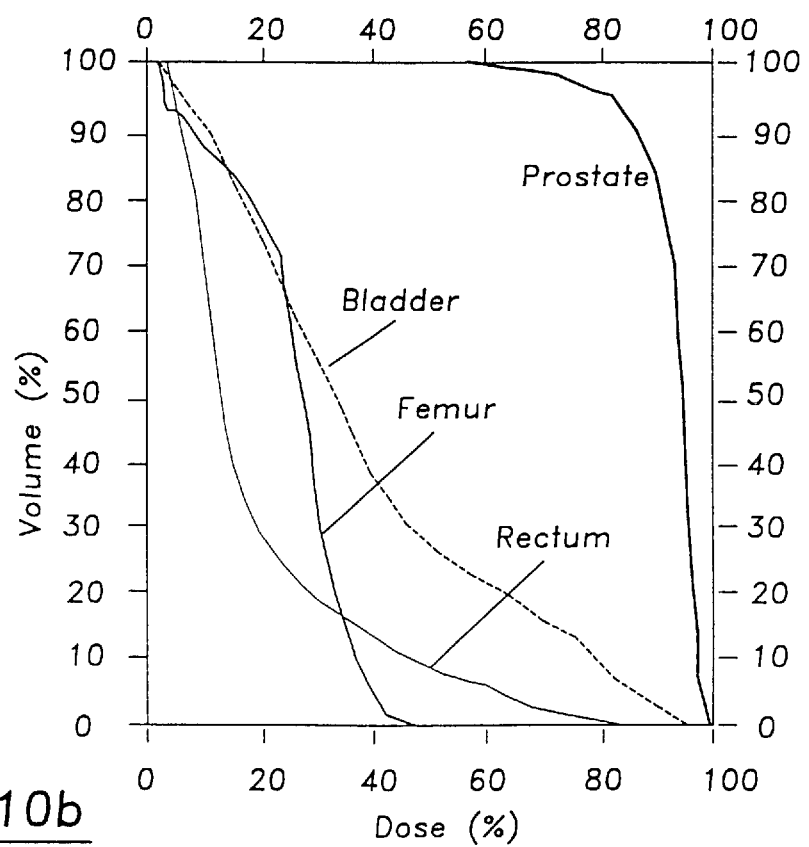

FIG. 10a is a view of prostate treatment geometry as in FIG. 9a but having beam intensity limited to ten levels. FIG. 10b is a dose-volume histogram for the prostate treatment geometry of FIG. 10a.

As illustrated by the histograms of FIGS. 9b and 10b, little difference is seen between the two intensity levels. It is therefore believed that when the number of intensity levels is included in the optimization process, no more than five levels are needed for intensity modulated arc therapy treatments.

Finally, it should be understood that the dose-volume histograms or subsequently derived biological scores depend on the total number of strata. This is defined as the product of the number of beams and the intensity levels within each beam. The number of intensity levels required to obtain optimal dose distribution is reduced as the number of beams increases.

EXAMPLE—PROSTATE TREATMENT PLAN

Figure 11:
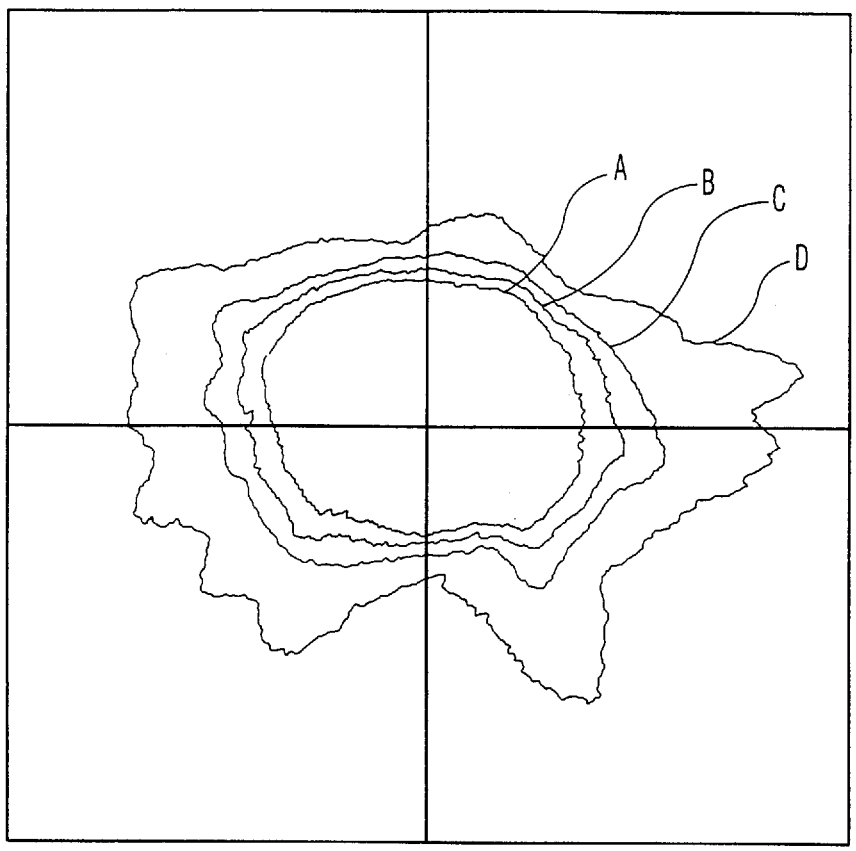
FIG. 11 illustrates a prostate treatment plan.

FIG. 11 illustrates a treatment plan application as used for treatment of a diseased prostate. A series of iso-dose lines A, B, C, and D represent various intensity levels. More particularly, the iso-dose line A represents 100% intensity, iso-dose line B represents 90% intensity, iso-dose line C represents 80% intensity, and iso-dose line D represents 50% intensity.

Those skilled in the art can appreciate the various advantages which may be obtained from the use of this invention and that modification may be made without departing from the true spirit of the invention after studying the specification, drawings and following claims.

I claim:

1. A method of performing radiation treatment on a patient, the method comprising the steps of:
   positioning the patient on a supporting structure;
   positioning a radiation-delivering apparatus at a first position;
   causing said radiation-delivering apparatus to produce a radiation field having a preselected shape;
   rotating said radiation-delivering apparatus about the patient along multiple superimposing arcs while changing the radiation field shape produced by said radiation-delivering apparatus in a synchronized manner by slaving rotation and changes in field shape to delivered radiation monitor units.

2. The method of performing radiation treatment according to claim 1, wherein one rotation about the patient by said radiation-delivering apparatus defines one arc.

3. The method of performing radiation treatment according to claim 1, including the step of varying the field shape during rotation to focus radiation doses on one or more tumor sites.

4. The method of performing radiation treatment according to claim 1, the method being used to irradiate a tumor, the method including the step of varying the field shape during rotation to substantially irradiate an irregularly-shaped tumor.

5. The method of performing radiation treatment according to claim 1, wherein multiple superimposing arcs are used to achieve desired three-dimensional dose distributions in a patient.

6. The method of performing radiation treatment according to claim 5, wherein each of said arcs may use a different "start" position and a different "stop" position.

7. The method of performing radiation treatment according to claim 5, including the step of adjusting said patient supporting structure so that said arcs are non-coplanar.

8. The method of performing radiation treatment according to claim 1, further including the step of calculating the minimum number of arcs required such that the desired dose distribution is delivered in a minimal amount of treatment time.

9. The method of performing radiation treatment according to claim 1, including the step of coordinating changes in irradiation delivery amount, field shape, and rotation.

10. The method of performing radiation treatment according to claim 1, including the step of changing field shapes in response to the amount of radiation delivered.

11. The method of performing radiation treatment according to claim 9, including the step of enslaving both the gantry rotation and field shape change to the radiation output of the radiation generating device.

12. The method of performing radiation treatment according to claim 2, including the step of effecting multiple radiation beam angles.

13. The method of performing radiation treatment according to claim 12, including the step of translating beam intensity distributions into multiple arcs from the intensity distributions at all said multiple beam angles required to deliver the desired dose distribution.

14. The method of performing radiation treatment according to claim 13, the radiation-delivering apparatus including a multi-leaf collimator, the multi-leaf collimator including a plurality of opposed and adjustable veins, the method including the step of determining the angle of said multi-leaf collimator veins along which the radiation fields are conformed such that the filed shape formed by the veins substantially matches the preferred field shape for all beam angles.

15. The method of performing radiation treatment according to claim 14, including the step of segmenting the two-dimensional beam intensity distributions of all beam angles into multiple, one-dimensional beam intensity distributions, each aligned with an opposed pair of multi-leaf collimator veins.

16. The method of performing radiation treatment according to claim 15, including the step of determining the opening of each opposed pair of veins and the sequence of opening so as to minimize required vein movement between two successive beam angles.

17. The method of performing radiation treatment according to claim 16, including the step of forming from the sets of the vein openings a stack of field shapes for all beam angles.

18. The method of performing radiation treatment according to claim 17, including the step of constructing arcs from said stack of field shapes by selecting one shape from each beam angle.

19. The method of performing radiation treatment according to claim 13, including the step of varying the field shape according to beam angle.

20. The method of performing radiation treatment according to claim 13, including the step of arbitrarily varying the range of arcs according to desired intensity distributions.

21. The method of performing radiation treatment according to claim 5, the method being used to irradiate a tumor, the method including the step of utilizing multiple arcs to superimpose radiation at a plurality of angles to conform the effective accumulated radiation dose to the shape of the tumor.

22. A method of performing radiation treatment on a patient, the method comprising the steps of:
   positioning the patient on a supporting structure;
   positioning a radiation-delivering apparatus at a first position;
   causing said radiation-delivering apparatus to produce a radiation field; and
   rotating said radiation-delivering apparatus about the patient along multiple superimposing arcs while causing said radiation field to vary in shape in a synchronized manner by slaving rotation and changes in field shape to delivered radiation monitor units to substantially irradiate an irregularly-shaped tumor.

23. The method of performing radiation treatment according to claim 22, including the step of varying the field shape during rotation to focus radiation doses on at least two tumor sites.

24. An apparatus for performing radiation treatment on a patient, the apparatus including:
   a housing containing a radiation-generating source;
   an outlet for allowing the passage of generated radiation, the outlet including a multi-leaf collimator for selectively altering the shape of the passing radiation;
   means associated with said housing for selectively altering the intensity of generated radiation;
   means for selectively rotating said housing around the patient along multiple superimposing arcs in a synchronized manner by slaving rotation and changes in shape of the passing radiation to delivered radiation monitor units; and
   means for selectively moving said housing along the long axis of the patient.

25. An apparatus for performing radiation treatment on a patient, the apparatus including:
   a housing containing a radiation-generating source;
   an outlet for allowing the passage of generated radiation, the outlet including means for selectively altering the shape of the passing radiation;
   means associated with said housing for selectively altering the intensity of generated radiation;
   means for selectively rotating said housing around the patient along multiple superimposing arcs in a synchronized manner by slaving rotation and changes in shape of the passing radiation to delivered radiation monitor units;
   means for selectively moving said housing along the long axis of the patient; and
   a data processing and system control unit operatively associated therewith for selectively controlling operation of said apparatus.

* * * * *